US00PP29991P2

(12) United States Plant Patent
Rigney

(10) Patent No.: US PP29,991 P2
(45) Date of Patent: Dec. 18, 2018

(54) ***WEIGELA* PLANT NAMED 'MONRIGNEY'**

(50) Latin Name: *Weigela florida*
Varietal Denomination: MONRIGNEY

(71) Applicant: Ken Rigney, South Hampton (GB)

(72) Inventor: Ken Rigney, South Hampton (GB)

( * ) Notice: Subject to any disclaimer, the term of this patent is extended or adjusted under 35 U.S.C. 154(b) by 0 days.

(21) Appl. No.: 15/731,371

(22) Filed: Jun. 2, 2017

(51) Int. Cl.
*A01H 5/00* (2018.01)

(52) U.S. Cl.
USPC ..... Plt./226
CPC ..... *A01H 5/00* (2013.01)

(58) Field of Classification Search
USPC ..... Plt./226
CPC ..... A01H 5/02; A01H 5/00
See application file for complete search history.

(56) References Cited

PUBLICATIONS https://www.amerinursery.com/plants/new-plants-2017-monrovia/; Dec. 2, 2016; 15 pages.*

* cited by examiner

*Primary Examiner* — Kent L Bell
(74) *Attorney, Agent, or Firm* — Cassandra Bright

(57) ABSTRACT

A new and distinct *Weigela* cultivar named 'MONRIGNEY' is disclosed, characterized by deep yellow foliage and deep red-purple flowers and buds. The new variety tolerates low temperatures to USDA Zone 3 and resists foliage scorch. The new variety is a *Weigela*, normally produced as an outdoor garden or container plant.

1 Drawing Sheet

Latin name of the genus and species: *Weigela florida*.
Variety denomination: 'MONRIGNEY'.

BACKGROUND OF THE INVENTION

The new *Weigela* cultivar is a product of a planned breeding program conducted by the inventor, Ken Rigney in his garden in South Hampton, United Kingdom. The objective of the breeding program was to produce new *Weigela* varieties with unique ornamental habits. The inventor has no record of when open pollination resulting in this new variety occurred.

The new variety was identified as a potentially interesting selection in April 2001 by the inventor. He discovered the interesting seedling in a planting of undistributed, unpatented proprietary seedlings resulting from his breeding program. The exact parents cannot be identified.

Asexual reproduction of the new cultivar 'MONRIGNEY' by softwood cuttings was first performed during June of 2001 at in the inventor's garden in South Hampton, United Kingdom. Subsequent asexual propagation has shown that the unique features of this cultivar are stable and reproduced true to type in 4 successive generations.

SUMMARY OF THE INVENTION

The cultivar 'MONRIGNEY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MONRIGNEY' These characteristics in combination distinguish 'MONRIGNEY' as a new and distinct *Weigela* cultivar:

1. Bright yellow foliage, significantly deeper yellow than known varieties.
2. Excellent hardiness, observed hardy to zone 3, while similar *Weigela* are observed hardy to zones 4 or 5.
3. Foliage does not scorch or burn in the full Sun.
4. Deep red-purple flowers and buds.

PARENT COMPARISON

The parent varieties cannot be identified.

COMMERCIAL COMPARISON

Plants of the new cultivar 'MONRIGNEY' can be compared to the commercial variety *Weigela florida* 'Briant Rubidor', unpatented. These varieties are similar in most horticultural characteristics, however, 'MONRIGNEY' differs in the following:

1. The new variety has darker yellow foliage.
2. The new variety has foliage which does not scorch.
3. The new variety has a deeper bud and bloom color.
4. Foliage of the new variety maintains its deep yellow color through Fall.

Plants of the new cultivar 'MONRIGNEY' can be compared to the commercial variety *Weigela florida* 'Carlton', U.S. Plant Pat. No. 20,025. These varieties are similar in most horticultural characteristics, however, 'MONRIGNEY' differs in the following:

1. The new variety has darker yellow foliage.
2. The new variety has foliage which does not scorch, 'Carlton' requires shade.
3. The new variety blooms more heavily and has a stronger rebloom.
4. Plants of the new variety are more upright in growth habit.

BRIEF DESCRIPTION OF THE PHOTOGRAPH

The accompanying photograph illustrates in full color typical foliage and flowers of 'MONRIGNEY' grown in a greenhouse, in Salem, Oreg. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MONRIGNEY' plants grown in a commercial nursery in Salem Oreg. The description is of plants during Spring of 2017. The plants were 2 years old and in 2 gallon containers. The growing temperature ranged from −31° C. to 38° C. Measurements and numerical values represent averages of typical plant types.

Botanical classification: *Weigela florida* 'MONRIGNEY'.

PROPAGATION

Time to initiate roots: About 15 days at approximately 27° C.

Root description: Fine, thin and freely branching.

Time to produce a rooted young plant: About 2 months at 27° C.

PLANT

Plant type: Shrub perennial.

Age of plant described: Approximately 2 years old.

Growth habit: Compact with good branching.

Pot size of plant described: 2 gallon pot.

Height: Approximately 80 cm to top of foliage.

Plant spread: Approximately 70 cm.

Growth rate: Medium.

Plant vigor: Strong.

Branching characteristics: Good, significant amount of basal and internodal branching.

Length of primary lateral branches: Approximately 20 to 35 cm.

Diameter of lateral branches: Approximately 8 to 14 mm.

Quantity of lateral branches: About 12.

Stem:

- *Stem appearance.*—Rounded with ridges on opposite side 180° apart, on pubescent stem.
- *Stem color.*—Near RHS Brown 200B.
- *Pubescence.*—Yes, predominately on the ridges.
- *Aspect.*—Straight, occurring at an angle of approximately 40-45°.

Internode length: Average range 2.0-3.5 cm.

FOLIAGE

Leaf:

- *Arrangement.*—Opposite.
- *Durability of foliage to stress.*—Very durable.
- *Quantity.*—Approximately 12 to 20 fully expanded per main branch.
- *Average length.*—Approximately 4.1 cm.
- *Average width.*—Approximately 2.4 cm.
- *Shape of blade.*—Ovate-oblanceolate.
- *Apex.*—Acute.
- *Base.*—Attenuate.
- *Attachment.*—Stalked.
- *Margin.*—Serrulate.
- *Texture of top surface.*—Slightly pubescence, soft.
- *Texture of bottom surface.*—More pubescence than upper side, feels rougher and slightly gritty.
- *Color.*—Young foliage upper side: Near RHS Yellow 8A. Young foliage under side: Near RHS Yellow 8A. Mature foliage upper side: Near RHS Yellow 2B. Mature foliage under side: Near RHS Yellow 2B.
- *Venation.*—Type: Pinnate. Venation color upper side: Near Yellow 9A. Venation color under side: Near RHS Yellow 10B.
- *Petiole.*—Average Length: Approximately 5 mm. Diameter: Connection to leaf: 1 mm; Connecting to stem: 3 mm. Petiole color upper side: Near RHS Yellow 12B. Petiole color lower side: Near RHS Yellow 12B. Petiole Texture upper side: Pubescent. Petiole Texture lower side: Pubescent.

FLOWER

Natural flowering season: Early to late Spring.

Flower arrangement: Single salverform flowers, mostly terminal.

Inflorescence type and habit: Umbel.

Quantity of flowers per inflorescence: Average range 4-8.

Inflorescence size:

- *Width.*—Approximately 4 cm.
- *Height.*—Approximately 6.5 cm.

Individual flowers:

- *Flower form.*—Salverform.
- *Flower aspect.*—Upright and slightly outward.
- *Size.*—Diameter: Approximately 1 cm. Length: Approximately 3.0 mm. Tube length: 1.6 cm. Tube base diameter: 3 mm. Flower throat diameter, top: 3 mm.
- *Flower other characteristics.*—Flower tube color: Lightly shaded near RHS Red 54C. Flower throat color: Near Red 53B. Persistence: Self cleaning. Fragrance: None.

Petal:

- *Petal arrangement.*—Whorl of petals fused at opening of throat.
- *Number of petals per flower.*—4.
- *Petal appearance.*—Smooth, slight color variation.
- *Petal shape.*—Rounded-orbicular.
- *Margin.*—Entire, slightly undulate.
- *Tip shape.*—Obtuse.
- *Length.*—1.2 cm.
- *Width.*—9 mm.
- *Texture.*—Upper: Smooth, soft, delicate. Lower: Smooth, soft, delicate. Throat; Soft, smooth.

Petal color:

- *When opening.*—Upper surface: Near RHS Red-Purple 59B. Lower surface: Near RHS Red-purple 59D.
- *Fully opened.*—Upper surface: Near RHS Red-Purple 58A. Lower surface: Near RHS Red-Purple 58A.
- *Petal vein color.*—Upper side: Near RHS Red 53A. Lower Side: Near RHS Red 53C.

Bud:
*Shape*.—Obovate.
*Length*.—Approximately 3.1 cm.
*Diameter*.—Approximately 9 mm.
*Color*.—Near RHS Red-Purple 61A.
Sepals:
*Shape*.—Narrow deltate.
*Arrangement*.—Unguiculate, fused at base.
*Number of sepal*.—5.
*Length*.—Approximately 8 mm.
*Width*.—Approximately 3 mm.
*Calyx shape*.—Uniguiculate.
*Margin*.—Entire.
*Base*.—Obtuse.
*Tip*.—Acuminate.
*Texture*.—Smooth, conaceous.
*Color*.—Upper side: Near RHS Red 53C. Lower side: Near RHS Red-53C.
Pedicel:
*Length*.—Average 1.0 to 1.7 cm.
*Diameter*.—2 mm.
*Color*.—Near RHS Red 47C.
*Strength*.—Good.
*Texture*.—Smooth, coriaceous, slightly pubescent.
Peuncle: No true peduncle, inflorescence arises from branch.

REPRODUCTIVE ORGANS

Stamens:
*Number*.—5.
*Filament length: Approximately* 1.2 cm.
*Filament color*.—Near RHS White 155A blended with Red-purple 58A.
Anthers:
*Shape*.—Linear, slightly oblong.
*Length*.—Approximately 8 mm.
*Color*.—Near RHS Greyed-yellow 161D.
*Pollen*.—Not observed.
Pistil:
*Number*.—1.
*Length*.—Approximately 2.5 cm.
*Style*.—Length: Approximately 3 cm. Color: Near RHS white 155A blended with Red-purple 58A.
*Stigma*.—Shape: Globular, flat-bottomed, lobed. Color: Near RHS Greyed-yellow 160D. Ovary color: Near RHS Red-purple 59A.

OTHER CHARACTERISTICS

Seeds and fruits: Not observed to date.
Garden performance: Excellent.
Disease/pest resistance: Good mildew resistance.
Temperature tolerance: The new variety tolerates temperatures with USDA Zones 3 through 8.

What is claimed is:

1. A new and distinct cultivar of *Weigela* plant named 'MONRIGNEY' as herein illustrated and described.

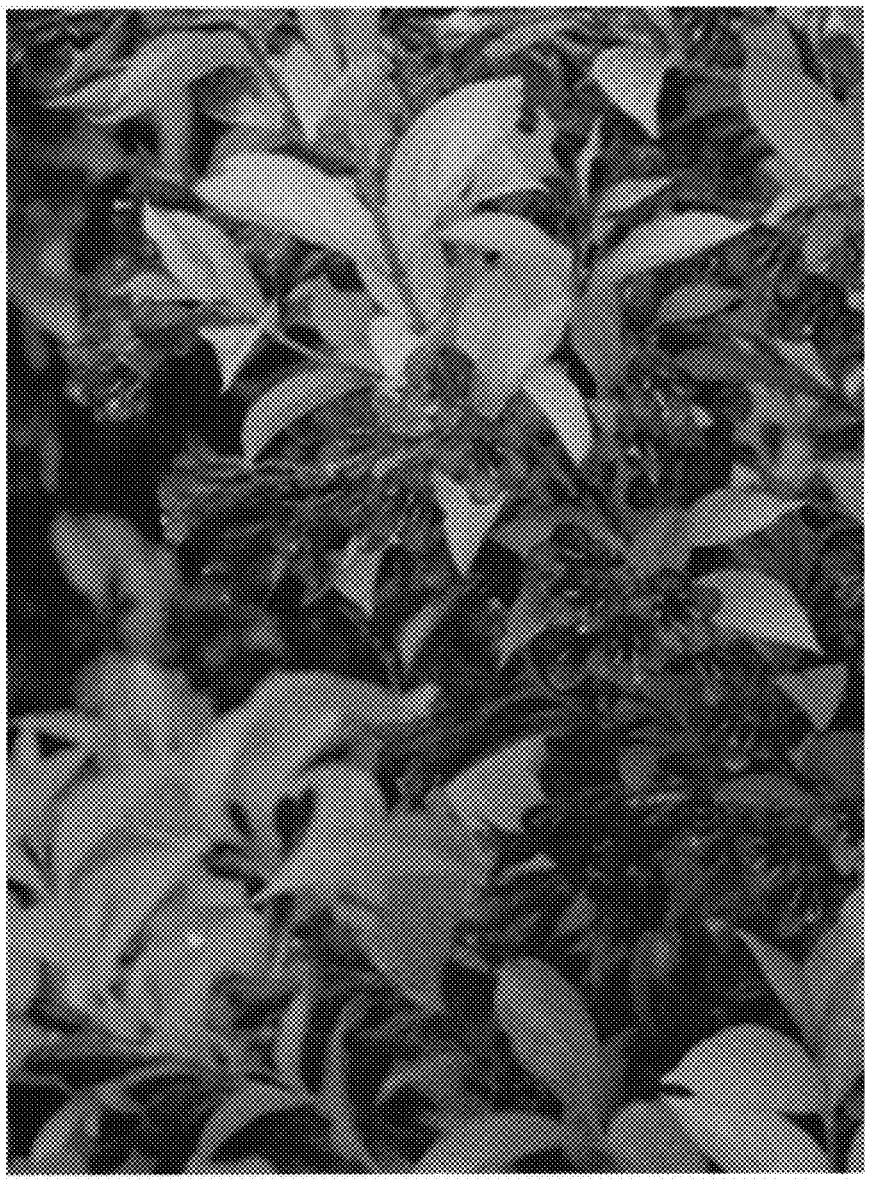

* * * * *